United States Patent [19]

Dillon

[11] Patent Number: 4,849,285
[45] Date of Patent: Jul. 18, 1989

[54] COMPOSITE MACROSTRUCTURE OF CERAMIC AND ORGANIC BIOMATERIALS

[75] Inventor: Mark E. Dillon, Watertown, Mass.

[73] Assignee: Bio Med Sciences, Inc., Amherst, N.Y.

[21] Appl. No.: 56,386

[22] Filed: Jun. 1, 1987

[51] Int. Cl.$^4$ .................. B32B 5/16; B32B 15/00; B32B 27/14; A61F 2/28

[52] U.S. Cl. .................... 428/330; 428/422; 623/11; 623/13; 623/16; 623/18; 623/23

[58] Field of Search .............. 428/422, 330; 623/11, 623/13, 16, 16 D, 18, 23

[56] References Cited

U.S. PATENT DOCUMENTS

| | | |
|---|---|---|
| 3,992,725 | 11/1976 | Homsy . |
| 4,129,470 | 12/1978 | Homsy . |
| 4,321,711 | 3/1982 | Mano ................................. 623/11 |
| 4,413,359 | 11/1983 | Akiyama et al. ................. 623/11 |
| 4,416,814 | 11/1983 | Battista ............................. 623/11 X |
| 4,536,179 | 8/1985 | Anderson et al. ................ 623/11 X |
| 4,576,608 | 3/1986 | Homsy ............................. 623/13 X |
| 4,629,464 | 12/1986 | Takata et al. .................... 623/16 |
| 4,664,669 | 3/1987 | Ohyabu et al. ................... 623/11 X |
| 4,693,986 | 9/1987 | Vit et al. .......................... 623/16 X |

FOREIGN PATENT DOCUMENTS

| | | | |
|---|---|---|---|
| 3301122A | 7/1984 | Fed. Rep. of Germany ... | 623/16 D |
| 12649 | 1/1983 | Japan ................................ | 623/16 D |
| 101145 | 6/1984 | Japan ................................ | 623/16 D |
| 1455360 | 11/1976 | United Kingdom ............. | 623/16 D |

OTHER PUBLICATIONS

Boretos, John W., Advances Ceramic Materials, vol. 2, No. 1, 1987, pp. 17, 18.

Primary Examiner—Marion E. McCamish
Assistant Examiner—M. A. Katz
Attorney, Agent, or Firm—Paul & Paul

[57] ABSTRACT

A composite self-supporting flexible agglomerated macrostructure is described which comprises (1) a matrix of unfibrillated polytetrafluoroethylene resin and addition curable silicone and (2) particulate material including hydroxyapatite and/or tricalcium phosphate uniformly distributed throughout said matrix, the macrostructure being uniformly permeated by a network of open pores formed in the process of manufacture by intimately blending particulate sodium chloride and subsequently leaching the sodium chloride particles.

6 Claims, No Drawings

COMPOSITE MACROSTRUCTURE OF CERAMIC AND ORGANIC BIOMATERIALS

This invention relates to the field of biomaterials, more particularly to the field of bioceramic materials and most particularly to the field of composites of ceramic and organic biomaterials.

A biomaterial is a substance designed for implantation within or incorporation with a living system, which includes for example anything that is intermittently or continuously exposed to body fluids although they may actually be located outside of the body proper.

Biomaterials in the form of surgical implants have been manufactured from metals, plastic, rubber, textiles, ceramics and certain composites thereof. Since bioceramic materials can exist in either inert, surface-active or resorbable forms, the uses of such materials are manifold, such as for example artificial heart valves, knee and hip joint prostheses, alveolar ridge reconstructions, tooth/root implants, percutaneous access devices, bone plates and artificial tendons. Inert bioceramic materials are used for heart valves and electronic implants, for example, where durability, impermeability and lack of physiological response are needed. The term "inert" refers to materials that are essentially stable with little or no tissue reactivity when implanted within the living organism. Surface-active bioceramic materials possess chemical reactivity with the physiological environment. As healing of the incision or wound site occurs, a simultaneous chemical bond between the tissue and the implant surface is stimulated. For example, bone will bond to dense hydroxyapatite (HA). Resorbable bioceramic materials are temporary space fillers or scaffolds for new tissue to develop. Natural tissue reconstruction occurs simultaneously with resorption. For example, tricalcium phosphate (TCP), having the formula $Ca_3(PO_4)_2$ is biocompatible, has the ability to promote the ingrowth of soft tissue and bone, especially in the porous state, and is bioresorbable.

Sintered polytetrafluoroethylene (PTFE) has been used as a biomaterial in various forms, such as sutures and solid implants. PTFE biomaterials are desirable because of their low density, minimal time-dependent degradation characteristics, minimal deterioration in vivo, ease of shaping, pliability and ability to be dry sterilized. There are no antibody or thrombogenic reactions around PTFE implant sites.

Medical-grade silicone rubber is a known biomaterial which when vulcanized is resilient, easily fabricated, physiologically inert, capable of being dry sterilized and has low modulii of elasticity.

Biomaterials are disclosed in U.S. Pat. Nos. 3,992,725 and 4,129,470, which are porous reinforced structures comprising stainless steel, vitreous carbon, alumina, zirconia, or other ceramic fibers bonded together by "sintered" polytetrafluoroethylene. The exposed surfaces of this material are said to have sufficiently high surface tension to be highly blood wettable and therefore suitable for ingrowth of tissues.

It is an object of this invention to provide a composite of disparate biomaterials that is self-supporting without the necessity of fibrous or fibrillated reinforcement.

It is a further object of this invention to provide a composite of organic and inorganic biomaterials wherein the organic biomaterial constitutes a matrix throughout which the inorganic biomaterial is uniformly distributed.

It is a further object of this invention to provide a composite of disparate biomaterials that is self-supporting without the necessity of fibrous of fibrillated reinforcement and which contains open pores.

I have now discovered a self-supporting, porous flexible composite of known organic and inorganic biomaterials that does not depend upon fibrous or fibrillated materials for reinforcement. The present self-supporting composite can be readily shaped by molding, carving or abrading into sized products which embody the corresponding properties of the component biomaterials.

The composite composition of this invention is a self-supporting flexible agglomerated macrostructure comprising (1) a matrix consisting essentially of a blend of sintered unfibrillated polytetrafluoroethylene resin and an addition cured silicone, said blend having been heated sufficiently to sinter the polytetrafluoroethylene and to cure said silicone composition; and (2) a particulate material selected from the class consisting of hydroxyapatite and tricalcium phosphate, said particulate material having a maximum size of about 2,000 microns, and being uniformly distributed throughout said matrix; said macrostructure being uniformly permeated by a network of open pores.

The process of manufacturing the composite material of this invention comprises the steps of (1) intimately blending a mixture of a major amount of unsintered and unfibrillated particulate polytetrafluoroethylene resin and minor amounts of (A) a hydrocarbon liquid and (B) an addition curable silicone composition containing a crosslinking catalyst, (2) intimately blending with the product of step (1) a particulate ceramic material selected from the class consisting of apatite and tricalcium phosphate and particulate sodium chloride, (3) introducing portions of the product of step (2) into opposing streams of air within a mill so as to form a homogeneous particulate mixture, (4) subjecting the product of step (3) to mechanical pressure, (5) while maintaining pressure subjecting the product of step (4) to a temperature sufficient to sinter polytetrafluoroethylene and to cure said silicone composition, and (6) solubilizing the particulate sodium chloride so as to create a network of open pores in the product of step (5) corresponding in size to the original sodium chloride particles. The particulate sodium chloride particles may have a maximum particle size of about 2,000 microns.

DESCRIPTION OF THE PREFERRED EMBODIMENTS

Example 1

29.44 grams (9.11 cc) of apatite (calcium phosphate-tribasic basic—Fisher Scientific Company) powder was fired at 12000° C. for 4 hours, then ground and sifted to a particle size distribution of:
  25% between 180 and 250 microns
  25% between 90 and 180 microns
  25% between 53 and 90 microns
  25% below 53 microns 1.51 grams (0.479 cc) of tricalcium phosphate was synthesized by the following series of reactions: (confirmed by X-ray diffraction analysis)

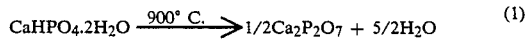

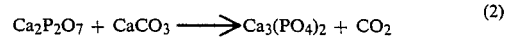

51.92 grams (23.98 cc) of sodium chloride (biological grade—Fisher Scientific Company) was ground and sifted to a particle size distribution of:
25% between [180 and 250 microns
50% between 90 and 180 microns
25% between 53 and 90 microns 3.28 grams (2.88 cc) of Silastic ® MDX4-4210 addition curable silicone elastomer (Dow Corning Corporation) was mixed into 3.64 grams (4.60 cc) of kerosene (Fisher Scientific Company) using a high sheer blender. The silicone ingredients comprised a 10/1 ratio of base to catalyst. The resultant solution was then slowly added to 25.30 grams (11.5 cc) of molding grade Teflon ® 7A polytetrafluoroethylene (E. I. dupont de Nemours and Company, Inc.) and jar tumbled for 8 hours. The apatite, tricalcium phosphate and sodium chloride particulates were then added and the mixture tumbled for an additional 4 hours. The resultant blend of inorganic and organic materials was then introduced into an operating Trost Air Mill at 40 psi air pressure. This mill utilizes opposing jets of air to cause the material to impact against itself. At this air pressure, little or no size reduction of the particulate matter occurs. Within a period of two hours (to prevent curing of the silicone resin), the air-milled mixture was pressed between plates in a cylindrical die about two inches deep and 2.5 inches in diameter at room temperature to about 5,000 psi pressure. This pressed form was then hot pressed at 340° C. and 2,000 psi to "sinter" the polytetrafluoroethylene and cure (vulcanize) the silicone elastomer. After cooling, the hot pressed material was submerged in a reservoir of distilled water to dissolve the sodium chloride component particulates, thereby creating a network of open pores with a size distribution corresponding to that of the original salt crystals. The leaching treatment was performed over a period of 48 hours while maintaining a water solution rich in $Ca^{++}$ and $PO_4^{-}$ ions in order to inhibit dissolution of the tricalcium phosphate component. Finally, the leached composite material was dried at a temperature below 100° C.

The product produced by the procedure of Example 1 was in the form of a cylindrical disc with smooth exterior surfaces. The 2.5 inch disc is pliable and resilient in the hands. Extreme tearing force applied by hand causes jagged disruption of the composite with the exposed broken internal edges having a homogeneous appearance.

The proportions of the starting materials utilized in Example 1 were chosen to effect a final composition of 60 volume percent organic materials and 40 volume percent ceramic materials, with an overall porosity of 50 volume percent. The open pores may have a maximum dimension of about 2,000 microns. The ceramic phase is 5 volume percent tricalcium phosphate and 95 volume percent apatite. The organic phase is 20 volume percent silicone rubber and 80 volume percent polytetrafluoroethylene.

Polytetrafluoroethylene (PTFE) in its virgin resin state is on the order of 95 percent crystalline, unless it has been "sintered". The word "sintered" is used in this application to describe the action of heating PTFE above its crystalline melting point and then cooling it. Because of its extremely high melt viscosity, the molten PTFE retains some of its amorphous structure when quenched. This creates a condition known as "amorphous locking" which promotes dimensional and chemical stability. This invention however does not involve the well-known processes of solid state sintering or vitreous sintering. Therefore, the bioceramic materials utilized in accordance with the composite of this invention remain particulate within the organic matrix formed by the "sintered" PTFE and the cured (vulcanized) silicone elastomer.

I claim:

1. A composite self-supporting flexible agglomerated macrostructure comprising (1) a matric consisting essentially of a blend of a major portion of unfibrillated polytetrafluoroethylene resin and a minor portion of an addition curable silicone composition, said blend having been heated sufficiently to sinter the polytetrafluoroethylene and to cure said silicone composition, and (2) a particulate material selected from the class consisting of hydroxyapatite and tricalcium phosphate, said particulate material having a maximum particle size of about 2,000 microns and being uniformly distributed throughout said matrix; said macrostructure being uniformly permeated by a network of open pores having a maximum pore size of about 2,000 microns and an overall porosity of up to about 50 percent by volume; and wherein said matrix comprises a major portion of said macrostructure and said particulate material comprises a minor portion of said macrostructure.

2. The composite macrostructure of claim 1, wherein the particulate material is hydroxyapatite.

3. The composite macrostructure of claim 1, wherein the particulate material is tricalcium phosphate.

4. The composite macrostructure of claim 1, wherein the particulate material is a mixture of hydroxyapatite and tricalcium phosphate.

5. The composite macrostructure of claim 1, wherein the particulate material has a particle size distribution between about 53 microns and 250 microns.

6. The composite macrostructure of claim 1, wherein the open pores range in size from about 53 microns to about 250 microns.

* * * * *

UNITED STATES PATENT OFFICE
CERTIFICATE OF CORRECTION

Patent No. 4,849,285                                    Dated July 18, 1989

Inventor(s) Mark E. Dillon

It is certified that error appears in the above-identified patent and that said Letters Patent is hereby corrected as shown below:

Col. 2, line 53, the word "basic" is printed twice;

Col. 2, line 54, "12000 " should be "1200 ";

Col. 3, line 4, "[" preceeding 180 should be deleted;

Col. 4, line 23, "matric" should be "matrix".

Signed and Sealed this

Nineteenth Day of November, 1991

Attest:

HARRY F. MANBECK, JR.

*Attesting Officer*         *Commissioner of Patents and Trademarks*